United States Patent [19]
Ushio et al.

[11] Patent Number: 5,880,291
[45] Date of Patent: Mar. 9, 1999

[54] PROCESS FOR PRODUCING OPTICALLY ACTIVE AZETIDINE-2-CARBOXYLIC ACID

[75] Inventors: Hideki Ushio; Naoyuki Takano, both of Takatsuki; Yukihiro Honda, Ashiya; Shinzo Seko; Motoo Hazama, both of Toyonaka, all of Japan

[73] Assignee: Sumitomo Chemical Company, Limited, Osaka, Japan

[21] Appl. No.: 924,320

[22] Filed: Sep. 5, 1997

[30] Foreign Application Priority Data

Sep. 6, 1996 [JP] Japan .................................. 8-236208
Nov. 19, 1996 [JP] Japan .................................. 8-307947

[51] Int. Cl.[6] ................................................. C07D 205/04
[52] U.S. Cl. ............................................................ 548/953
[58] Field of Search ............................................. 548/953

[56] References Cited

U.S. PATENT DOCUMENTS

| | | | |
|---|---|---|---|
| 4,721,793 | 1/1988 | Mason et al. | 548/953 |
| 4,855,452 | 8/1989 | Verbrugge et al. | 548/953 |
| 4,946,839 | 8/1990 | Kozikowskip et al. | 548/953 X |

FOREIGN PATENT DOCUMENTS

0279543A1  8/1988  European Pat. Off. .

OTHER PUBLICATIONS

"A Facile New Synthesis of DL–Azetidine–2–Carboxylic Acid (1a)" by R. Rodebaugh et al., Dept of Chemistry University of Nebraska, Communication to the Editor, Jun. 1969 pp. 435–437.

"Synthesis and x–ray analysis of 1–{(1S)–phenylethyl}–azetidine–(2R)–piperidinamide" by R. De Gelder et al., Chemical Abstracts No. 126:117844q, vol. 126, No. 9, Mar. 3, 1997.

R. M. Rodebaugh et al., *Resolution of DL–Azetidine– 2–carboxylic Acid*,J. Heterocyclic Chem, vol. 6, pp. 993–994 (1969).

R. M. Rodebaugh et al., *A Facile New Synthesis of DL–Azetidine–2–carboxylic Acid (1a)*, J. Heterocyclic Chem, vol. 6, pp. 435–437, 1969.

A. P. Kozikowski et al., *Synthesis of Metabotropic Receptor Activity of the Novel Rigidified Glutamate Analogues (+)–and (–)–trans–Azetidine–2,4–dicarboxylic Acid and their N–Methyl Derivatives*, J. Med. Chem., vol. 36, pp. 2706–2708 (1993).

M. Miyoshi et al., *A Novel Synthesis of Optically Active Azetidine–2–carboxylic Acid*, Chemistry Letters, pp. 5–6 (1973).

N. H. Cromwell et al., *The Azetidines. Recent Synthetic Developments*, Chemical Reviews, vol. 79, No. 4, pp. 331–358 (1979).

Gelder et al., "Synthesis and X–ray analysis . . . ", *J. of Chem. Crystallography*, vol. 26, No. 9, 1996 pp. 639–642.

*Primary Examiner*—Fiona T. Powers
*Attorney, Agent, or Firm*—Birch, Stewart, Kolasch & Birch, LLP

[57] ABSTRACT

The present invention provides a process for preparing optically active azetidine-2-carboxylic acids using readily available reagents of relatively low price in the industry. Thus, there is provided optically active azetidine-2-carboxylic acid, and a process for producing the same by subjecting optically active N-(alkylbenzyl)azetidine-2-carboxylic acid represented by the formula (1):

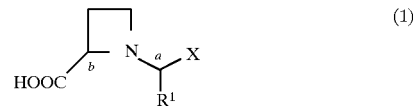

to hydrogenolysis in the presence of a catalyst.

12 Claims, No Drawings

PROCESS FOR PRODUCING OPTICALLY ACTIVE AZETIDINE-2-CARBOXYLIC ACID

FIELD OF THE INVENTION

The present invention relates to a process for producing optically active azetidine-2-carboxylic acid and an intermediate for producing the same.

The optically active azetidine-2-carboxylic acid has been known as an intermediate for producing a pharmaceutical such as an antithrombotic agent disclosed in EP 542525.

Optically active azetidine-2-carboxylic acid has been produced by a process which has the steps of;

a) reacting azetidine-2-carboxylic acid, which is obtained by a process disclosed in Journal of Heterocyclic Chemistry, 6, 435 (1969), with benzyloxycarbonyl chloride to give N-(benzyloxycarbonyl)-azetidine-2-carboxylic acid, b) subjecting N-(benzyloxycarbonyl)-azetidine-2-carboxylic acid to optical resolution using an optically active tyrosine hydrazide, and then c) subjecting the obtained optically active N-(benzyloxycarbonyl)-azetidine-2-carboxylic acid to hydrogenolysis to give an optically active azetidine-2-carboxylic acid [Journal of Heterocyclic Chemistry, 6, 993 (1969)].

The prior art method for preparing optically active azetidine-2-carboxylic acid, however, had difficulties in that it requires, as a reagent for optical resolution, an optically active tyrosine hydrazide which is expensive and not readily available on the industrial scale.

As a result of extensive research, the present inventors have found optically active N-(alkylbenzyl)azetidine-2-carboxylic acid which can be readily converted to the desired optically active azetidine-2-carboxylic acid by a hydrogenolysis reaction; and a process for producing optically active N-(alkylbenzyl) azetidine-2-carboxylic acid or an ester thereof through an efficient optical resolution using readily available dicarboxylic acid, whereby completing the present invention.

Thus, the present invention provides:

1. optically active N-(alkylbenzyl)azetidine-2-carboxylic acid represented by the formula (1):

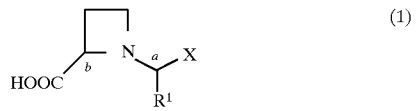

wherein $R^1$ is an alkyl group having 1 to 6 carbon atoms,
X is a phenyl group which may be substituted with at least one group selected from a halogen atom, a hydroxyl group, an alkyl group having 1 to 6 carbon atoms and an alkoxy group having 1 to 6 carbon atoms; and
a and b independently designate asymmetric carbon atoms;

2. a process for producing optically active azetidine-2-carboxylic acid, which comprises: subjecting the optically active N-(alkylbenzyl)azetidine-2-carboxylic acid represented by the formula (1) as defined above to hydrogenolysis in the presence of a catalyst.

3. a process for producing optically active N-(alkylbenzyl)azetidine-2-carboxylic acid represented by the formula (1) as defined above, which comprises hydrolyzing optically active N-(alkylbenzyl) azetidine-2-carboxylic acid ester represented by the formula (2):

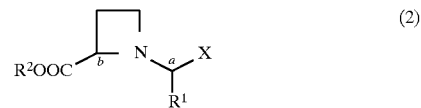

wherein $R^2$ is an aryl group or a saturated hydrocarbon group which may be substituted with an aryl group and X, $R^1$, a and b have the same meaning as defined above, in the presence of an acid or a base.

4. a process for producing optically active N-(alkylbenzyl)azetidine-2-carboxylic acid ester represented by the formula (2) as defined above, which comprises the steps of:

(a) contacting N-(alkylbenzyl)azetidine-2-carboxylic acid ester represented by the formula (2)':

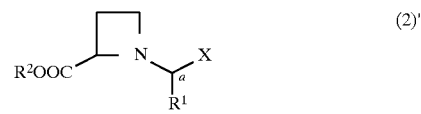

wherein $R^1$, $R^2$, X and a have the same meaning as defined above, with a dicarboxylic acid of the formula (5):

wherein B is a single bond, a phenylene group,
a straight or branched chain alkylene group which may be substituted with a phenyl group, a hydroxy group which may be protected or a halogen atom,
a cyclic alkylene group which may be substituted with a hydroxy group which may be protected, a halogen atom or a phenyl group, or
a straight or branched chain alkenylene group which may be substituted with a phenyl group, to obtain an adduct of the formula (6):

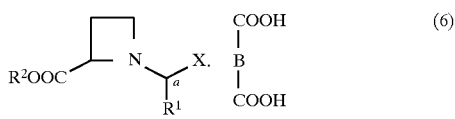

wherein $R^1$, $R^2$, X, B and a have the same meaning as defined above, (b) isolating dicarboxylic acid salt of optically active N-(alkylbenzyl)azetidine-2-carboxylic acid ester represented by the formula (7):

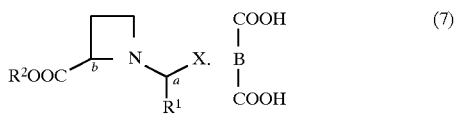

wherein X, B, $R^1$, $R^2$, a and b have the same meaning as defined above, and (c) treating the obtained salt of the formula (7) with a base.

5. a process for producing optically active N-(alkylbenzyl)azetidine-2-carboxylic acid ester represented by the formula (2) as defined above, which comprises the steps of:

(a) contacting N-(alkylbenzyl)azetidine-2-carboxylic acid ester represented by the formula (2)':

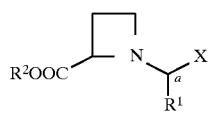

wherein $R^1$, $R^2$, X and a have the same meaning as defined above, with a chiral dicarboxylic acid, (b) isolating diastereomer salt comprising the chiral dicarboxylic acid and optically active N-(alkylbenzyl) azetidine-2-carboxylic acid ester represented by the formula (2) as defined above, and (c) treating the obtained diastereomer salt with a base.

First a description will be made to the first aspect of the present invention, which relates to optically active N-(alkylbenzyl)azetidine-2-carboxylic acid represented by the formula (1) as defined above.

In the optically active N-(alkylbenzyl)azetidine-2-carboxylic acid represented by the formula (1), examples of the alkyl group represented by the substituent $R^1$ include a methyl group, an ethyl group, a propyl group, an isopropyl group, a butyl group, a tert-butyl group and the like.

X is a phenyl group which may be substituted with at least one group selected from a halogen atom, a hydroxyl group, an alkyl group having 1 to 6 carbon atoms and an alkoxy group having 1 to 6 carbon atoms.

Examples of the alkyl group include a methyl group, an ethyl group, a propyl group, an isopropyl group, a butyl group, a tert-butyl group and the like.

Examples of the halogen atom include a chlorine atom, a bromine atom, an iodine atom and a fluorine atom.

Examples of the alkoxy group include a methoxy group, an ethoxy group and the like, respectively.

In formula (1) above and other formulae of (2), (2)', (4), (6) and (7), a and b each independently designate an asymmetric carbon atom having S or R configuration.

Examples of the optically active N-(alkylbenzyl) azetidine-2-carboxylic acid represented by the formula (1) include optically active isomers of N-(1-methylbenzyl)azetidine-2-carboxylic acid, N-(1-phenylpropyl)azetidine-2-carboxylic acid, N-[1-(p-tolyl)ethyl]azetidine-2-carboxylic acid, N-[1-(p-chlorophenyl)ethyl]azetidine-2-carboxylic acid, N-[1-(2,4-dichlorophenyl)ethyl]azetidine-2-carboxylic acid, N-[1-(p-methoxyphenyl)ethyl]azetidine-2-carboxylic acid, or N-[1-(4-hyoxyphenyl)ethyl]azetidine-2-carboxylic acid.

Specific examples are: N-[(S)-methylbenzyl]azetidine-2-(S)-carboxylic acid, N-[(S)-methylbenzyl]azetidine-2-(R)-carboxylic acid, N-[(R)-methylbenzyl]azetidine-2-(R)-carboxylic acid, and N-[(R)-methylbenzyl]azetidine-2-(S)-carboxylic acid.

According to the present invention, the optically active N-(alkylbenzyl)azetidine-2-carboxylic acid represented by the formula (1) can readily be converted to an optically active azetidine-2-carboxylic acid in high yield by hydrogenolysis in the presence of a catalyst.

Next a description will be made to the process for producing optically active azetidine-2-carboxylic acid, which comprises subjecting the compound of the formula (1) as defined above to hydrogenolysis in the presence of a catalyst.

Such a catalyst includes, for example, platinum on carbon, platinum black, palladium on carbon, palladium hydroxide on carbon, palladium acetate, palladium chloride, palladium oxide or palladium hydroxide. Palladium hydroxide or Palladium hydroxide on carbon is preferred. The amount of the catalyst to be used is within a range usually of 0.0001 to 0.5 times, by the weight, of the optically active N-(alkylbenzyl) azetidine-2-carboxylic acid represented by the formula (1).

For the hydrogenolysis reaction, a reducing agent, for example, hydrogen, hydrazine or its salt such as hydrochloride, carbonate, formic acid or its salt such as an ammonium salt and the like can be used.

In the reaction, usually a solvent is used. The solvent includes, for example, water;

alcohol solvents such as methanol, ethanol, 2-propanol and the like;

ester solvents such as ethyl acetate, methyl acetate, butyl acetate and the like;

nitrile solvents such as acetonitrile and the like;

aromatic hydrocarbon solvents such as toluene, xylene, benzene and the like;

aliphatic hydrocarbon solvents such as hexane, heptane and the like;

halogenated hydrocarbon solvents such as dichloromethane, dichloroethane, chloroform, chlorobenzene, o-dichlorobenzene and the like;

ether solvents such as diethyl ether, tert-butyl methyl ether and the like; and amide solvents such as acetamide, N,N-dimethylformamide, N,N-dimethylacetamide and the like.

These solvents can be used independently or as a mixture thereof. The amount of the solvent to be used is not particularly limited, and are usually used in an amount within a range of 0.5 to 100 times, by weight, of the optically active N-(alkylbenzyl)azetidine-2-carboxylic acid represented by the formula (1).

When hydrogen gas is used in the hydrogenolysis reaction, it is usually introduced by bubbling into the reaction mixture of optically active N-(alkylbenzyl)azetidine-2-carboxylic acid represented by the formula (1) and the catalyst while stirring the reaction mixture under hydrogen atmosphere at an ordinary or elevated pressure.

When a reducing agent other than hydrogen gas is employed in the hydrogenolysis reaction, the reducing agent is usually added to a mixture of optically active N-(alkylbenzyl)azetidine-2-carboxylic acid represented by the formula (1) and the catalyst.

In both cases, the reaction temperature is usually within a range of −50° to 200° C.

The optically active azetidine-2-carboxylic acid can readily be isolated from the reaction solution after completion of reaction by a conventional method. For example, the catalyst is filtered off and then the solvent is evaporated from the filtrate to yield the product. The product may be further purified by recrystallization, column chromatography or the like, if necessary.

The hydrogenolysis reaction proceeds with retention of configuration at the asymmetric carbon atom designated by b in the optically active N-(alkylbenzyl)azetidine-2-carboxylic acid represented by the formula (1).

The N-(alkylbenzyl)azetidine-2-carboxylic acid represented by the formula (1) can readily be prepared by hydrolyzing optically active N-(alkylbenzyl)azetidine-2-carboxylic acid ester represented by the formula (2):

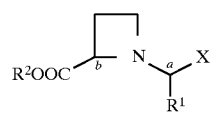

wherein $R^2$ is an aryl group or a saturated hydrocarbon group which may be substituted with an aryl group and X, $R^1$ and a and b have the same meaning as defined above, in the presence of an acid or a base.

The aryl group represented by $R^2$ includes phenyl group or the like; and the saturated hydrocarbon group which may be substituted with an aryl group includes an alkyl group having 1 to 10 carbon atoms such as a methyl group, an ethyl group, a propyl group, an isopropyl group, a butyl group, an octyl group and the like; and alicyclic group having 3 to 10 carbon atoms such as a menthyl group, an isomenthyl group, a borryl group, an isobornyl group and the like.

Said alkyl group may be substituted with an aryl group such as phenyl group, tolyl group and the like.

Examples of the optically active N-(alkylbenzyl) azetidine-2-carboxylic acid ester represented by the formula (2) include optically active isomers of: methyl N-(1-methylbenzyl)azetidine-2-carboxylate, ethyl N-(1-methylbenzyl)azetidine-2-carboxylate, butyl N-(1-methylbenzyl)azetidine-2-carboxylate, octyl N-(1-methylbenzyl)azetidine-2-carboxylate, isopropyl N-(1-methylbenzyl)azetidine-2-carboxylate, benzyl N-(1-methylbenzyl) azetidine-2-carboxylate, methylbenzyl N-(1-methylbenzyl) azetidine-2-carboxylate, phenethyl N-(1-methylbenzyl) azetidine-2-carboxylate, phenyl N-(1-methylbenzyl)azetidine-2-carboxylate, bornyl N-(-methylbenzyl)azetidine-2-carboxylate, isobornyl N-(1-methylbenzyl)azetidine-2-carboxylate, menthyl N-(1-methylbenzyl)azetidine-2-carboxylate, isomenthyl N-(1-methylbenzyl)azetidine-2-carboxylate, methyl N-(1-phenylpropyl)azetidine-2-carboxylate, ethyl N-(1-phenylpropyl)azetidine-2-carboxylate, butyl N-(1-phenylpropyl)azetidine-2-carboxylate, octyl N-(1-phenylpropyl)azetidine-2-carboxylate, isopropyl N-(1-phenylpropyl)azetidine-2-carboxylate, benzyl N-(1-phenylpropyl)azetidine-2-carboxylate, methylbenzyl N-(1-phenylpropyl)azetidine-2-carboxylate, phenethyl N-(1-phenylpropyl)azetidine-2-carboxylate, phenyl N-(1-phenylpropyl)azetidine-2-carboxylate, bornyl N-(1-phenylpropyl)azetidine-2-carboxylate, isobornyl N-(1-phenylpropyl)azetidine-2-carboxylate, menthyl N-(1-phenylpropyl)azetidine-2-carboxylate, isomenthyl N-(1-phenylpropyl)azetidine-2-carboxylate, methyl N-[1-(p-tolyl)ethyl]azetidine-2-carboxylate, ethyl N-[1-(p-tolyl)ethyl]azetidine-2-carboxylate, butyl N-[1-(p-tolyl)ethyl] azetidine-2-carboxylate, octyl N-[1-(p-tolyl)ethyl]azetidine-2-carboxylate, isopropyl N-[1-(p-tolyl)ethyl]azetidine-2-carboxylate, benzyl N-[1-(p-tolyl)ethyl]azetidine-2-carboxylate, methylbenzyl N-[1-(p-tolyl)ethyl]azetidine-2-carboxylate, phenethyl N-[1-(p-tolyl)ethyl]azetidine-2-carboxylate, phenyl N-[1-(p-tolyl)ethyl]azetidine-2-carboxylate, bornyl N-[1-(p-tolyl)ethyl]azetidine-2-carboxylate, isobornyl N-[1-(p-tolyl)ethyl]azetidine-2-carboxylate, menthyl N-[1-(p-tolyl)ethyl]azetidine-2-carboxylate, isomenthyl N-[1-(p-tolyl)ethyl)azetidine-2-carboxylate, methyl N-[1-(p-chlorophenyl)ethyl]azetidine-2-carboxylate, ethyl N-[1-(p-chlorophenyl)ethyl]azetidine-2-carboxylate, butyl N-[1-(p-chlorophenyl)ethyl]azetidine-2-carboxylate, octyl N-[1-(p-chlorophenyl)ethyl]azetidine-2-carboxylate, isopropyl N-[1-(p-chlorophenyl)ethyl] azetidine-2-carboxylate, benzyl N-[1-(p-chlorophenyl) ethyl]azetidine-2-carboxylate, methylbenzyl N-[1-(p-chlorophenyl)ethyl]azetidine-2-carboxylate, phenethyl N-[1-(p-chlorophenyl)ethyl]azetidine-2-carboxylate, phenyl N-[1-(p-chlorophenyl)ethyl]azetidine-2-carboxylate, bornyl N-[1-(p-chlorophenyl) ethyl]azetidine-2-carboxylate, isobornyl N-[1 -(p-chlorophenyl)ethyl]azetidine-2-carboxylate, menthyl N-[ 1-(p-chlorophenyl)ethyl] azetidine-2-carboxylate, isomenthyl N-[1-(p-chlorophenyl) ethyl]azetidine-2-carboxylate, methyl N-[1-(2,4-dichlorophenyl)ethyl]azetidine-2-carboxylate, ethyl N-[1-(2,4-dichlorophenyl)ethyl]azetidine-2-carboxylate, butyl N-[1-(2,4-dichlorophenyl)ethyl]azetidine-2-carboxylate, octyl N-[1-(2,4-dichlorophenyl)ethyl]azetidine-2-carboxylate, isopropyl N-[1-(2,4-dichlorophenyl)ethyl] azetidine-2-carboxylate, benzyl N-[1-(2,4-dichlorophenyl) ethyl]azetidine-2-carboxylate, methylbenzyl N-[1-(2,4-dichlorophenyl)ethyl]azetidine-2-carboxylate, phenethyl N-[1-(2,4-dichlorophenyl)ethyl]azetidine-2-carboxylate, phenyl N-[1-(2,4-dichlorophenyl)ethyl]azetidine-2-carboxylate, bornyl N-[1-(2,4-dichlorophenyl)ethyl] azetidine-2-carboxylate, isobornyl N-[1-(2,4-dichlorophenyl)ethyl]azetidine-2-carboxylate, menthyl N-[1-(2,4-dichlorophenyl)ethyl]azetidine-2-carboxylate, isomenthyl N-[1-(2,4-dichlorophenyl)ethyl]azetidine-2-carboxylate, methyl N-1-(p-methoxyphenyl)ethyl]azetidine-2-carboxylate, ethyl N-[1-(p-methoxyphenyl)ethyl] azetidine-2-carboxylate, butyl N-[1-(p-methoxyphenyl) ethyl]azetidine-2-carboxylate, octyl N-[1-(p-methoxyphenyl)ethyl]azetidine-2-carboxylate, isopropyl N-[1-(p-methoxyphenyl)ethyl]azetidine-2-carboxylate, benzyl N-[1-(p-methoxyphenyl)ethyl]azetidine-2-carboxylate, methylbenzyl N-[1-(p-methoxyphenyl)ethyl]azetidine-2-carboxylate, phenethyl N-[1-(p-methoxyphenyl)ethyl] azetidine-2-carboxylate, phenyl N-[1-(p-methoxyphenyl) ethyl]azetidine-2-carboxylate, bornyl N-1-(p-methoxyphenyl)ethyl]azetidine-2-carboxylate, isobornyl N-[1-(p-methoxyphenyl)ethyl]azetidine-2-carboxylate, menthyl N-[1-(p-methoxyphenyl)ethyl]azetidine-2-carboxylate, isomenthyl N-[1-(p-methoxyphenyl)ethyl] azetidine-2-carboxylate, methyl N-[1-(4-hyoxyphenyl) ethyl]azetidine-2-carboxylate, ethyl N-[1-(4-hyoxyphenyl) ethyl]azetidine-2-carboxylate, butyl N-[1-(4-hyoxyphenyl) ethyl]azetidine-2-carboxylate, octyl N-[1-(4-hyoxyphenyl) ethyl]azetidine-2-carboxylate, isopropyl N-[1-(4-hyoxyphenyl)ethyl]azetidine-2-carboxylate, benzyl N-[1-(4-hyoxyphenyl)ethyl]azetidine-2-carboxylate, methylbenzyl N-[1-(4-hyoxyphenyl)ethyl]azetidine-2-carboxylate, phenethyl N-[1-(4-hyoxyphenyl)ethyl] azetidine-2-carboxylate, bornyl N-[1-(4-hyoxyphenyl)ethyl] azetidine-2-carboxylate, bornyl N-[1-(4-hyoxyphenyl)ethyl] azetidine-2-carboxylate, isobornyl N-[1-(4-hyoxyphenyl) ethyl]azetidine-2-carboxylate, menthyl N-[1-(4-hyoxyphenyl)ethyl]azetidine-2-carboxylate, and isomenthyl N-[1-(4-hyoxyphenyl)ethyl]azetidine-2-carboxylate.

These optically active N-(alkylbenzyl)azetidine-2-carboxylic acid ester represented by the formula (2) may be used in the form of salts such as hydrochloride, phosphate or the like.

The acid to be used in the hydrolysis includes, for example, inorganic acids such as hydrochloric acid, sulfuric acid, phosphoric acid and the like; and organic acids such as methanesulfonic acid, p-toluenesulfonic acid, acetic acid, 2-ethylhexanoic acid, benzoic acid, trifluoroacetic acid and the like.

The base to be used in the hydrolysis includes, for example, alkali metal hydroxides such as lithium hydroxide, sodium hydroxide, potassium hydroxide and the like;

alkaline earth metal hydroxides such as barium hydroxide, calcium hydroxide and the like;

alkali metal carbonates such as sodium carbonate, potassium carbonate and the like;

alkali metal hydrogen carbonates such as sodium hydrogen carbonate, potassium hydrogen carbonate and the like; and alkoxides such as sodium methoxide, potassium tert-butoxide and the like.

The acid or base is used in an amount within a range usually of 0.1 to 20 moles per mole, preferably of 0.1 to 5 moles per mole of the optically active N-(alkylbenzyl) azetidine-2-carboxylic acid ester represented by the formula (2). Water is usually used in an amount within a range of 1 to 100 times, by weight, of the optically active N-(alkylbenzyl)azetidine-2-carboxylic acid ester represented by the formula (2).

An organic solvent can be used in the hydrolysis reaction. Said organic solvent is not particularly limited insofar as it does not adversely affect the reaction and includes: for example, alcohol solvents such as methanol, ethanol, 2-propanol and the like;

nitrile solvents such as acetonitrile and the like;

hydrocarbon solvents such as toluene, benzene, xylene, hexane, heptane and the like;

halogenated hydrocarbon solvents such as dichloromethane, dichloroethane, chloroform, chlorobenzene, o-dichlorobenzene and the like;

ether solvents such as diethyl ether, tert-butyl methyl ether and the like;

amide solvents such as acetamide, N,N-dimethylformamide, N,N-dimethylacetamide and the like;

nitro compound solvents such as nitrobenzene, nitromethane and the like;

sulfoxide solvents such as dimethylsolfoxide and the like.

The reaction is usually carried out by mixing the optically active N-(alkylbenzyl)azetidine-2-carboxylic acid ester represented by the formula (2) with an acid or a base in water. The reaction temperature is within a range usually of −50° to 200° C., preferably of −20° to 150° C.

The optically active N-(alkylbenzyl)azetidine-2-carboxylic acid represented by the formula (1) can be isolated from the reaction mixture after hydrolysis reaction by a conventional method, for example, evaporation of the solvent from the reaction mixture, neutralization of the reaction mixture, extraction or the like.

For example, a volatile acid such as acetic acid is used for hydrolysis, the desired optically active N-[alkylbenzyl] azetidine-2-carboxylic acid can be obtained by evaporating acetic acid from the resulting reaction mixture. When a nonvolatile acid or an acid having high boiling point such as 2-ethylhexanoic acid, stearic acid or benzoic acid is used, the desired acid can be obtained by evaporating aqueous layer separated from the reaction mixture after extraction of the reaction mixture with an organic solvent which are not miscible with water. Alternatively, the N-[alkylbenzyl] azetidine-2-carboxylic acid may be used in the sebsequent process without isolating.

When the acid or base used in the hydrolysis reaction forms an insoluble salt with an acid or a base used for neutralization of the reaction mixture, such a insoluble salt can be removed first, and then the resulting solution can be subjected to a usual post treatment.

The hydrolysis reaction proceeds with retention of configuration at the asymmetric carbon atom designated by a or b in the optically active N-(alkylbenzyl)azetidine-2-carboxylic acid represented by the formula (2).

Next a description will be made to the process for producing optically active N-(alkylbenzyl)azetidine-2-carboxylic acid ester represented by the formula (2) as defined above.

The process comprises the steps of:

(a) contacting the N-(alkylbenzyl)azetidine-2-carboxylic acid ester represented by the formula (2)' as defined above with a dicarboxylic acid of the formula (5) as defined above to obtain an adduct of the formula (6) as defined above, (b) isolating the dicarboxylic acid salt of optically active N-(alkylbenzyl)azetidine-2-carboxylic acid ester represented by the formula (7) as defined above, and (c) treating the obtained salt of the formula (7) with a base.

Dicarboxylic acid of the formula (5) will be explained below.

Examples of the straight or branched chain alkylene group represented by the substituent B include:

alkylene groups having 1 to 8 carbon atoms such as methylene group, an ethylene group, a propylene group, a butylene group, a hexylene group, octylene group and the like.

The straight or branched chain alkylene groups may be substituted with:

a hydroxy group which may be protected by a protecting group such as a methyl group, an ethyl group, a tert-butyl group, a benzyl group, a p-methoxybenzyl group, a methoxymethyl group, a benzyloxymethyl group, a benzoyl group, a trimethylsilyl group, a tert-butyldimethylsilyl group and the like; or a halogen atom such as a chlorine atom, a bromine atom, an iodine atom and a fluorine atom; or a phenyl group.

Examples of the alkylene group substituted with a phenyl group include, for example, a 2-phenyl-1,1-ethylene group.

Examples of the cyclic alkylene group include cyclic alkylene group having 3 to 10 carbon atoms such as a 2,2-dimethyl-1-methyl-1,3-cyclopentylene group, a 1,1-cyclopropylene group, a 1,1-cyclobutylene group, a 1,2-cyclopentylene group, a 1,2-cyclohexylene group, a 1,3-cyclohexylene group and the like, and these may be substituted with:

a hydroxy group which may be protected by a protecting group such as a methyl group, an ethyl group, a tert-butyl group, a benzyl group, a p-methoxybenzyl group, a methoxymethyl group, a benzyloxymethyl group, a benzoyl group, a trimethylsilyl group, a tert-butyldimethylsilyl group or the like;

a halogen atom such as a chlorine atom, a bromine atom, an iodine atom or a fluorine atom and the like; or a phenyl group.

Examples of the straight or branched chain alkenylene group include vinylene group, ethynylene group and the like and these may be substituted with a phenyl group.

Specific examples of the dicarboxylic acid represented by the formula (5) include aromatic or aliphatic dicarboxylic acids such as oxalic acid, malonic acid, succinic acid, glutaric acid, adipic acid, suberic acid, sebacic acid, camphoric acid, benzylmalonic acid, fumaric acid, maleic acid, acetylenedicarboxylic acid, phthalic acid, isophthalic acid, terephthalic acid, cyclopropanedicarboxylic acid, cyclobutanedicarboxylic acid, cyclopentanedicarboxylic acid, cyclohexanedicarboxylic acid and the like; oxygen-substituted dicarboxylic acids such as malic acid, dibenzoyltartaric acid, tartaric acid and the like; and halogen-substituted dicarboxylic acids such as 2,3-dichlorosuccinic acid, 2,3-dibromosuccinic acid and the like.

In the step (a) above, said dicarboxylic acid of the formula (5) is used in an amount within a range usually of 0.1 to 10 moles per mole, preferably of 0.1 to 2 moles per mole of the N-(alkylbenzyl)azetidine-2-carboxylic acid esters represented by the formula (2)'.

The step (a) can be carried out in the absence of a solvent. However, a solvent may be added, if necessary. The solvent that can be used includes, for example, water;

alcohol solvents such as methanol, ethanol, 2-propanol, butanol, ethyleneglycol and the like;

nitrile solvents such as acetonitrile and the like; hydrocarbon solvents such as toluene, benzene, xylene, hexane, heptane and the like;

halogenated hydrocarbon solvents such as dichloromethane, dichloroethane, chloroform, chlorobenzene, o-dichlorobenzene and the like;

ether solvents such as diethyl ether, dipropyl ether, dibutyl ether, tetrahydrofuran, tert-butyl methyl ether and the like;

amide solvents such as acetamide, N,N-dimethylformamide, N,N-dimethylacetamide and the like;

nitro compounds such as nitrobenzene, nitromethane and the like; and sulfoxides such as dimethylsulfoxide and the like.

These solvents can be used independently or as a mixture thereof. The amount of the solvent is not particularly limited but preferably such an amount of the solvent which enables good stirring of the mixture of the dicarboxylic acid and the compound of the formula (2)' is used. Such amount is usually within a range of 0.01 to 100 times, preferably of 0.01 to 20 times, by weight, of the N-(alkylbenzyl)azetidine-2-carboxylic acid esters represented by the formula (2)'.

The step (a) is carried out, for example, by contacting the diastereomeric mixture of N-(alkylbenzyl)azetidine-2-carboxylic acid esters with the dicarboxylic acid to obtain a product of the formula (6) under stirring, and in a solvent, if necessary. The mixing is usually conducted at a temperature range of −80° to 200° C., preferably of −20° to 100° C.

In this process, one of the diastereomers of N-(alkylbenzyl)azetidine-2-carboxylic acid ester predominantly forms a dicarboxylic acid salt of the formula (7) and precipitates. The precipitated salt can readily be isolated from the reaction mixture after completion of the reaction by a conventional method, such as, for example, by filtration.

One diastereomer of the N-(alkylbenzyl)azetidine-2-carboxylic acid ester may provide no suitable precipitated salt instantly to isolate depending on the conditions, for example, the use of an excess amount of the dicarboxylic acid, the solubility of a solvent, when used, or the properties of the salt to be precipitated. However, in such cases following methods can be applied to isolate the desired single diastereomer.

The salt of the desired single diastereomer can be crystallized or precipitated by such a conventional method of cooling the solution, adding seed crystals, vibrating, simply standing, or adding a solvent that has poor solubility to the desired salt. If a solvent is used, it is may be removed by evaporation. Then a suitable solvent that has poor solubility to the desired salt may be chosen for recrystallization.

Specific examples of such a solvent include:

an alcohol such as methanol, ethanol, 2-propanol, butanol, ethyleneglycol or the like;

a hydrocarbon such as toluene, benzene, xylene, hexane, heptane or the like; and an ether such as diethyl ether, dipropyl ether, dibutyl ether, tetrahydrofuran, tert-butyl methyl ether or the like.

Thus crystallized dicarboxylic acid salt of one diastereomer of N-(alkylbenzyl)azetidine-2-carboxylic acid ester and can readily be separated, for example, by filtration and may further be purified by an appropriate means such as recrystallization or the like, if necessary.

In the meantime, the salt of the other diastereomer contained in the filtrate mother liquor after the filtration can readily be recovered by a conventional method such as evaporation of the solvent, and the salt of the desired diastereomer may be further treated with a base to obtain the desired diastereomer.

The base to be used in step (c) includes, for example, alkali metal hydroxides such as lithium hydroxide, sodium hydroxide, potassium hydroxide and the like;

alkaline earth metal hydroxides such as calcium hydroxide and the like;

alkali metal carbonates such as sodium carbonate, potassium carbonate and the like;

alkali metal hydrogen carbonates such as sodium hydrogen carbonate, potassium hydrogen carbonate and the like;

alkaline earth metal hydrogen carbonates such as calcium hydrogen carbonate, phosphates such as disodium hydrogen phosphate, sodium dihydrogen phosphate, dipotassium hydrogen phosphate, potassium dihydrogen phosphate and the like; and organic bases such as triethylamine, tributylamine and the like.

The base can be used independently or as a mixture thereof and is usually used in an amount within a range of 0.1 to 10 moles per mole of the dicarboxylic acid salts of diastereomer of the N-[alkylbenzyl]azetidine-2-carboxylic acid ester.

After the treatment with the base, the desired optically active N-[alkylbenzyl]azetidine-2-carboxylic acid ester can readily be obtained from the reaction mixture by a conventional process, for example, extraction or the like.

A description will be made to a process for producing N-(alkylbenzyl)azetidine-2-carboxylic acid ester of the formula (2) as defined above, which comprises reacting di-substituted butyric acid ester represented by the formula (3):

wherein $Y^1$ and $Y^2$ are the same or different and are leaving groups and $R^2$ has the same meaning as defied above, with an optically active alkylbenzylamine represented by the formula (4):

wherein $R^1$, X and a have the same meaning as defined above, in the presence of a base.

In the di-substituted butyric acid ester represented by the formula (3), examples of the leaving group represented by the substituents $Y^1$ and $Y^2$ include halogen atoms such as a chlorine atom, a bromine atom and an iodine atom, a mesyloxy group, a tosyloxy group, a benzenesulfonyloxy group, a nitrobenzenesulfonyloxy group and the like.

Said di-substituted butyric acid ester includes, for example, dihalo-substituted butyric acid esters such as methyl 2,4-dichlorobutyrate, ethyl 2,4-dichlorobutyrate, butyl 2,4-dichlorobutyrate, octyl 2,4-dichlorobutyrate, isopropyl 2,4-dichlorobutyrate, benzyl 2,4-dichlorobutyrate, methylbenzyl 2,4-dichlorobutyrate, phenethyl 2,4-dichlorobutyrate, phenyl 2,4-dichlorobutyrate, menthyl 2,4-dichlorobutyrate, bornyl 2,4-dichlorobutyrate, isobornyl 2,4-dichlorobutyrate, methyl 2,4-dibromobutyrate, ethyl 2,4-dibromobutyrate, butyl 2,4-dibromobutyrate, octyl 2,4-dibromobutyrate, isopropyl 2,4-dibromobutrate, benzyl 2,4-dibromobutyrate, methylbenzyl 2,4-dibromobutyrate, phenethyl 2,4-dibromobutyrate, phenyl 2,4-dibromobutyrate, menthyl 2,4-dibromobutyrate, bornyl 2,4-dibromobutyrate, isobornyl 2,4-dibromobutyrate, methyl 2,4-diiodobutyrate, ethyl 2,4-diiodobutyrate, butyl 2,4-diiodobutyrate, octyl 2,4-diiodobutyrate, isopropyl 2,4-diiodobutyrate, benzyl 2,4-diiodobutyrate, methylbenzyl 2,4-diiodobutyrate, phenethyl 2,4-diiodobutyrate, phenyl 2,4-diiodobutyrate, menthyl 2,4-diiodobutyrate, bornyl 2,4-diiodobutyrate, isobornyl 2,4-diiodobutyrate, methyl 2,4-dimesyloxybutyrate, ethyl 2,4-dimesyloxybutyrate, butyl 2,4-dimesyloxybutyrate, octyl 2,4-dimesyloxybutyrate, isopropyl 2,4-dimesyloxybutyrate, benzyl 2,4-dimesyloxybutyrate, methylbenzyl 2,4-dimesyloxybutyrate, phenethyl 2,4-dimesyloxybutyrate, phenyl 2,4-dimesyloxybutyrate, methyl 2,4-ditosyloxybutyrate, ethyl 2,4-ditosyloxybutyrate, butyl 2,4-ditosyloxybutyrate, octyl 2,4-ditosyloxybutyrate, isopropyl 2,4-ditosyloxybutyrate, benzyl 2,4-ditosyloxybutyrate, methylbenzyl 2,4-ditosyloxybutyrate, phenethyl 2,4-ditosyloxybutyrate, phenyl 2,4-ditosyloxybutyrate, methyl 2,4-dibenzenesulfonyloxybutyrate, ethyl 2,4-dibenzenesulfonyloxybutyrate, butyl 2,4-dibenzenesulfonyloxybutyrate, octyl 2,4-dibenzenesulfonyloxybutyrate, isopropyl 2,4-dibenzenesulfonyloxybutyrate, benzyl 2,4-dibenzenesulfonyloxybutyrate, methylbenzyl 2,4-dibenzenesulfonyloxybutyrate, phenethyl 2,4-dibenzenesulfonyloxybutyrate, phenyl 2,4-dibenzenesulfonyloxybutyrate, methyl 2,4-di(nitrobenzenesulfonyloxy)butyrate, ethyl 2,4-di(nitrobenzenesulfonyloxy)butyrate, butyl 2,4-di(nitrobenzenesulfonyloxy)butyrate, octyl 2,4-di(nitrobenzenesulfonyloxy)butyrate, isopropyl 2,4-di(nitrobenzenesulfonyloxy)butyrate, benzyl 2,4-di(nitrobenzenesulfonyloxy)butyrate, methylbenzyl 2,4-di(nitrobenzenesulfonyloxy)butyrate, phenethyl 2,4-di(nitrobenzenesulfonyloxy)butyrate, phenyl 2,4-di(nitrobenzenesulfonyloxy)butyrate and the like.

The optically active alkylbenzylamine represented by the formula (4) incudes methylbenzylamine, 1-phenylpropylamine, 1-(p-tolyl)ethylamine, 1-(p-chlorophenyl)ethylamine, 1-(2,4-dichlorophenyl)ethylamine, 1-(p-methoxyphenyl)ethylamine, 1-(4-hydroxyphenyl)ethylamine and the like, among which (S)-methylbenzylamine and (R)-methylbenzylamine are preferred in view of availability.

The reaction of the di-substituted butyric acid ester represented by the formula (3) with the optically active alkylbenzylamine represented by the formula (4) may be carried out in the presence of a base.

The base include, for example, inorganic base including alkali metal hydroxides such as lithium hydroxide, sodium hydroxide, potassium hydroxide and the like;

alkaline earth metal hydroxides such as barium hydroxide, calcium hydroxide and the like;

carbonates such as sodium carbonate, potassium carbonate, sodium hydrogen carbonate, potassium hydrogen carbonate and the like;

organic bases such as triethylamine, pyridine, and the like.

The amount of the base to be used is usually in a range of 0.01 to 20 moles per mole, preferably of 0.01 to 5 moles per mole of the di-substituted butyric acid ester.

Alkylbenzylamine of the formula (4) as such may also be used as a base in this reaction, and the amount of the alkylbenzylamine to be used is usually 2 moles or more per mole of the disubstituted butyric acid ester of the formula (3).

Said react-on is usually carried out in a solvent. The solvent is not particularly limited insofar as it does not adversely affect the reaction and includes, for example, alcoholic solvents such as methanol, ethanol, 2-propanol and the like;

nitrile solvents such as acetonitrile and the like; hydrocarbon solvents such as toluene, benzene, xylene, hexane, heptane and the like;

halogenated hydrocarbon solvents such as dichloromethane, dichloroethane, chloroform, chlorobenzene, o-dichlorobenzene and the like;

ether solvents such as diethyl ether, tert-butyl methyl ether and the like;

amide solvents such as acetamide, N,N-dimethylformamide, N,N-dimethylacetamide and the like;

nitro compound solvents such as nitrobenzene, nitromethane and the like; and sulfoxide solvents such as dimethylsolfoxide and the like.

These solvents can be used independently or as a mixture thereof and are used in an amount within a range usually of 1 to 100 times, preferably 1 to 20 times, by weight, of the di-substituted butyric acid ester.

Said reaction is usually carried out by mixing the di-substituted butyric acid ester with the optically active alkylbenzylamine in a solvent.

The reaction temperature is within a range usually of −50° to 200° C. and preferably of −20° to 150° C. The optically active alkylbenzylamine is used in an amount within a range usually of 0.5 to 20 moles per mole, preferably of 0.5 to 5 moles per mole of the di-substituted butyric acid ester.

The diastereomeric mixture of the optically active N-(alkylbenzyl)azetidine-2-carboxylic acid esters after completion of the reaction, can be isolated from the reaction mixture by a conventional method. For example, the mixture is extracted with a hydrophobic organic solvent and the solvent is evaporated from the resulting organic layer.

The optically active N-(alkylbenzyl)azetidine-2-carboxylic acid ester can be isolated from the diastereomeric mixture by a conventional process. For example, the diastereomeric mixture is applied onto a chromatography column, or subjected to recrystallization, or the mixture may be dissolved in acidic water and the obtained aqueous solution may be extracted fractionally using hydrophobic solvents such as toluene, diethyl ether, hexane and the like while varying pH of the aqueous solution.

Preferably, the salt of the optically active azetidine-2-carboxylic acid ester with the dicarboxylic acid represented by the formula (7) can be obtained by reacting a compound of the formula (2)":

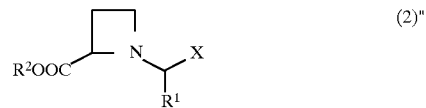
(2)"

wherein $R^1$, $R^2$ and X have the same meaning as defined above, with the chiral dicarboxylic acid in a manner similar to that described above, separating the desired diastereomer and treating the salt with a base. The chiral dicarboxylic acid to be used in said process includes any one of the optically active isomers of tartaric acid, dibenzoyltartaric acid, malic acid, camphoric acid or the like.

The compound of the formula (2)'' is obtained by reacting the di-substituted butyric acid ester represented by the above formula (3) with an alkylbenzylamine represented by the formula (4)':

wherein R¹ and X have the same meaning as defined above, in a manner similar to that described above.

EXAMPLES

The present invention will now be described in more detail by means of Examples, which should not be construed as a limitation upon the scope of the present invention.

Example 1

Into a solution of methyl (RS)-2,4-dibromobutyrate (48.53 g) dissolved in acetonitrile (400 ml) was added dropwise (S)-methylbenzylamine (67.87 g) at 50° C. and the mixture was stirred at the same temperature for 4 hours. Further, (S)-methylbenzylamine (2.26 g) was added at the same temperature and then the mixture was stirred at the same temperature for 6 hours. The mixture was concentrated under reduced pressure. The obtained residue was mixed with toluene (300 ml) and concentrated again under reduced pressure to remove acetonitrile. The obtained residue was combined with ether (300 ml) and the mixture was stirred for 2 hours. After standing, precipitated solid substance was filtered off and the filtrate was concentrated to give methyl N-[(S)-methylbenzyl]azetidine-2-(RS)-carboxylate (59.03 g, yield: 77.7%, brown oil).

The obtained methyl N-[(S)-methylbenzyl]azetidine-2-(RS)-carboxylate (10 g) was subjected to silica gel column chromatography (eluate: hexane/ethyl acetate=10/1) to give methyl N-[(S)-methylbenzyl]azetidine-2-(S)-carboxylate (4.8 g) and methyl N-[(S)-methylbenzyl]azetidine-2-(R)-carboxylate (4.68 g).
Methyl N-[(S)-methylbenzyl]azetidine-2-(S)-carboxylate:
  ¹H-NMR(CDCl₃), δ: 7.37–7.20 (m, 5 H); 3.76 (t, J=8.4 Hz, 1 H); 3.75 (s, 3 H); 3.45 (q, J=6.6 Hz, 1 H); 3.11 (td, J=7.6 Hz, J'=2.6 Hz,1 H); 2.80 (m, 1 H); 2.33–2.12 (m, 2 H); 1.22 (d, J=6.6 Hz, 3 H).
Methyl N-[(S)-methylbenzyl]azetidine-2-(R)-carboxylate:
  ¹H-NMR(CDCl₃), δ: 7.37–7.20 (m, 5 H); 3.61 (m, 2 H); 3.36 (q, J=6.6 Hz, 1 H); 3.33 (s, 3 H); 3.01 (m, 1 H); 2.35–2.10 (m, 2 H); 1.29 (d, J=6.5 Hz, 3 H).

Example 2

Into a solution of methyl (RS)-2,4-dibromobutyrate (48.53 g) dissolved in acetonitrile (400 ml) was added dropwise (R)-methylbenzylamine (67.87 g) at 50° C. and the mixture was stirred at the same temperature for 3.5 hours. The mixture was concentrated under reduced pressure. The obtained residue was mixed with toluene (200 ml) and concentrated again under reduced pressure to remove acetonitrile. The obtained residue was combined with hexane (500 ml) and the mixture was stirred for 6.5 hours. Precipitated solid substance was filtered off to give a filtrate and the solid substance.

The solid substance obtained above was dissolved in water (200 ml) and the liberated organic layer was separated to give the organic layer and an aqueous layer. The aqueous layer was extracted twice with toluene (50 ml) and the obtained organic layers were combined and further with the liberated organic layer.

The organic layer was further combined with the filtrate described above, the solvent was evaporated and the obtained residue was dissolved in toluene and washed with water. The toluene layer was analyzed by GC-IS to reveal that the layer contained 32.1 g of methyl N-[(R)-methylbenzyl]azetidine-2-(RS)-carboxylate. Yield: 78.3%.

Example 3

Into a solution of methyl (RS)-2,4-dibromobutyrate (37.49 g) dissolved in acetonitrile (650 ml) was added dropwise a solution of (S)-methylbenzylamine (94.86 g) in acetonitrile (100 ml) at 60° C. over 5.5 hours. The mixture was left to stand at room temperature for 16 hours and concentrated under reduced pressure. The obtained residue was mixed with toluene (200 ml) and concentrated again under reduced pressure to remove acetonitrile. The obtained residue was combined with ether (600 ml) and hexane (200 ml) and the mixture was stirred at room temperature for 24 hours. Precipitated solid substance was filtered off and the filtrate was concentrated. The obtained residue was mixed with toluene (80 ml) and extracted with 12% hydrochloric acid (100 ml). To the obtained aqueous layer was added 9% aqueous sodium hydrogen carbonate solution (110 ml) and extracted with toluene to form aqueous and organic layers. The aqueous layer had a pH of 4.5. The obtained organic layer was washed with water and the solvent was evaporated to leave a residue (20.96 g), which was distilled under reduced pressure to give methyl N-[(S)-methylbenzyl]azetidine-2-(RS)-carboxylate [13.8 g, pale yellow oil, yield: 43.4%, b.p. 103.5°–106° C. (0.2 mmHg)].

Analysis of this product by gas chromatography revealed that the ratio of methyl N-[(S)-methylbenzyl]azetidine-2-(S)-carboxylate and methyl N-[(S)-methylbenzyl]azetidine-2-(R)-carboxylate was 51/49.

To the aqueous layer of pH 4.5 obtained above was added 9% aqueous sodium hydrogen carbonate solution (50 ml) and extracted with toluene (50 ml) and then further amount of toluene (100 ml). Combined organic layer was washed with water and concentrated to give methyl N-[(S)-methylbenzyl]azetidine-2-(RS)-carboxylate (2.56 g).

Analysis of this product by gas chromatography revealed that the ratio of methyl N-[(S)-methylbenzyl]azetidine-2-(S)-carboxylate and methyl N-[(S)-methylbenzyl]azetidine-2-(R)-carboxylate was 85/15.

Example 4

Methyl N-[(S)-methylbenzyl]azetidine-2-(RS)-carboxylate (2.46 g) obtained in a manner similar to that in Example 1 was added to 5.6% aqueous barium hydroxide solution (34.7 g) and the mixture was stirred within a range of temperature of 94°–98° C. for 2 hours. Then, the mixture was washed twice with toluene (20 ml), once with ether (20 ml) and gaseous carbon dioxide was bubbled into the mixture at room temperature to precipitate barium carbonate. After stirring the mixture at 96° C. for 30 minute, barium carbonate was removed by filtration and the filtrate was concentrated to give N-[(S)-methylbenzyl]azetidine-2-(RS)-carboxylic acid, which was further subjected to silica gel column chromatography (eluate: chloroform/methanol=5/1–2/1) to give N-[(S)-methylbenzyl]azetidine-2-(S)-carboxylic acid (0.75 g, yield: 32.5%) and N-[(S)-methylbenzyl]azetidine-2-(R)-carboxylic acid (0.86 g, yield: 37.3%).
N-[(S)-methylbenzyl]azetidine-2-(S)-carboxylic acid:
  ¹H-NMR(CDCl₃), δ: 7.53–7.36 (m, 5 H); 6.28 (brs, 2 H); 4.40 (t, J=9.4 Hz, 1 H); 4.23 (q, J=6.9 Hz, 1 H); 3.88

(td, J=9.2 Hz, J'=4.0 Hz, 1 H); 3.34 (q, J=9.2 Hz, 1 H); 2.66 (m, 1 H); 2.43 (m, 1 H); 1.70 (d, J=6.9 Hz, 3 H).

N-[(S)-methylbenzyl]azetidine-2-(R)-carboxylic acid:

$^1$H-NMR(CDCl$_3$), δ: 7.46–7.27 (m, 5 H); 5.15 (brs, 2 H); 4.37 (t, J=8.7 Hz, 1 H); 4.16 (m, 2 H); 3.54 (m, 1 H); 2.41 (m, 2 H); 1.7 (d, J=6.6 Hz, 3 H).

Example 5

N-[(S)-methylbenzyl]azetidine-2-(S)-carboxylic acid (11.11 g) obtained in a manner similar to that in Example 4 and a catalyst (palladium hydroxide on carbon, content of palladium hydroxide: 10%) were added to a mixed solvent of ethanol (25 g) and water (25 g) and the mixture was stirred in a hydrogen atmosphere at 27° C. for 1 hour, heated to 40° C. and stirred further at the same temperature for 10 hours. After removing the catalyst by filtration, the filtrate was concentrated to give (S)-azetidinecarboxylic acid (5.22 g, yield: 99%, colorless crystals in 100% e.e. The value of e.e. was determined by high performance liquid chromatography analysis using a chiral column.

Example 6

Methyl N-[(S)-methylbenzyl]azetidine-2-carboxylate (0.27 g, the ratio: 2S isomer/2R isomer=52/48) and L-tartaric acid (0.15 g) were dissolved in methanol (6 ml) at room temperature. Then, the mixture was concentrated to give tartaric acid salt of methyl N-[(S)-methylbenzyl] azetidine-2-carboxylate, which was recrystallized from a mixed solvent of methyl tert-butyl ether (6 ml) and methanol (2 ml) to give crystals of tartaric acid salt of methyl N-[(S)-methylbenzyl]azetidine-2-(S)-carboxylate (0.12 g, colorless crystals, yield: 28%). $^1$H-NMR (DMSO), δ: 7.29 (m, 5 H); 4.39 (s, 2 H); 3.79 (t, J=8.3 Hz, 1 H); 3.70 (s, 3 H); 3.47 (q, J=6.3 Hz, 1 H); 3.00 (q, J=5.9 Hz, 1 H); 2.77 (q, J=7.6 Hz, 1 H); 2.18 (m, 2 H); 1.15 (d, J=6.3 Hz, 3 H).

The crystals were dissolved in a saturated aqueous sodium hydrogen carbonate solution, which was extracted with toluene. Analysis of the extract by GC revealed that the product had 99.7% d.e.

Example 7

A solution of methyl N-[(S)-methylbenzyl]azetidine-2-carboxylate (29.91 g, the ratio: 2S isomer/2R isomer=52/48) in methyl tert-butyl ether was added dropwise to a solution ofL-tartaric acid (16.55 g) in methanol (20.26 g) under reflux. Further, 21.43 g of methanol was added and the obtained homogeneous solution was cooled to 29° C. A small amount of the crystals obtained in Example 6 was fed as seed crystals to initiate crystallization. Then, after cooled to 5° C., crystals were collected by filtration, washed with methyl tert-butyl ether and dried in vacuo to give tartaric acid salt of methyl N-[(S)-methylbenzyl]azetidine-2-(S)-carboxylate (25.36 g, yield: 48%, 91% d.e.).

Example 8

Tartaric acid salt of methyl N-[(S)-methylbenzyl] azetidine-2-(S)-carboxylate (25.13 g) obtained in Example 7 was dissolved in methanol (126.24 g) under reflux and a part of methanol (79.3 g) was distilled off. Then, 70 g of methyl tert-butyl ether was added dropwise and the mixture was filtered at room temperature to give crystals. The obtained crystals were washed with methyl tert-butyl ether and dried in vacuo to give tartaric acid salt of methyl N-[(S)-methylbenzyl]azetidine-2-(S)-carboxylate (20.87 g, yield: 84%, 100% d.e.).

Example 9

The procedure in Example 7 was repeated in 1/5 scale except that toluene was used in place of methyl tert-butyl ether to give tartaric acid salt of methyl N-[(S)-methylbenzyl]azetidine-2-(S)-carboxylate (4.64 g, yield: 45%, 96% d.e.).

Example 10

The procedure in Example 6 was repeated except that 0.12 g of fumaric acid was used in place of L-tartaric acid to give fumaric acid salt of methyl N-[(S)-methylbenzyl]azetidine-2-(S)-carboxylate (colorless crystals, 0.04 g, yield: 12%, 98.1% d.e.).

Example 11

Into a solution of methyl (RS)-2, 4-dibromobutyrate (91.0 g) dissolved in toluene (77 g) was added dropwise (RS)-methylbenzylamine (45.3 g) at 75° C. over 2 hours. The mixture was left to stand at 90° C. for 12 hours. water (135 g) was added to the mixture and separated at 70° C., and the obtained organic layer was washed with water (50 g), 1% hydrochloric acid (40 g) and water (50 g). A sample of the obtained organic layer (185 g) was subjected to GC-IS analysis, which revealed yield of 76.1% and diastereomeric ratio of 51:49.

Example 12

200 g of 49.2% methyl N-[(RS)-methylbenzyl]azetidine-2-(RS)-carboxylate solution in toluene was added dropwise to a solution of L-tartaric acid (6.84 g) in methanol (10.26 g) at 60° C. 0.005 g of tartaric acid salt of methyl N-[(S)-methylbenzyl]azetidine-2-(S)-carboxylate was added as seed crystals to the mixture and was maintained at the temperature for 0.5 hour. To the resulting slurry was added 30 g of 50% methyl N-[(RS)-methylbenzyl]azetidine-2-(RS) -carboxylate in toluene solution was added dropwise at 60° C. over 1 hour. The slurry was cooled to 0° C. and crystals were collected by filtration. The obtained crystals were washed with cold methanol and dried in vacuo to give L-tartaric acid salt of methyl N-[(S)-methylbenzyl] azetidine-2-(S)-carboxylate (16.5 g, yield: 15.7%, 99.7% d.e.). The obtained crystals were treated in the following Example 14, 15 or 16 to yield (S)-azetidine-2-carboxylic acid. (>99% e.e).

Example 13

The reaction was conducted in a similar manner as conducted in Example 12 except that methyl N-[(S)-methylbenzyl]azetidine-2-(RS) -carboxylate was used in place of N-[(RS)-methylbenzyl]azetidine-2-(RS) -carboxylate and in a 5.5 times scale to give L-tartaric acid salt of methyl N-[(S)-methylbenzyl]azetidine-2-(S)-carboxylate (101.8 g, yield: 44%, 99.8% d.e.).

Example 14

20% aqueous sodium carbonate (623.2 g) was added dropwise to a mixture of L-tartaric acid salt of methyl N-[(S)-methylbenzyl]azetidine-2-(S)-carboxylate (425.5 g), water (425.5 g) and toluene (105 g). The reaction mixture was separated, and aqueous layer was extracted with toluene (105 g). The combined organic layer was washed twice with water (243 g×2), and concentrated under reduced presssure to give methyl N-[(S)-methylbenzyl]azetidine-2-(S)-carboxylate (249.2 g; Yield 98%).

Example 15

To a mixture of methyl N-[(S)-methylbenzyl]azetidine-2-(S)-carboxylate (161.6 g) and water (323 g) was added 2-ethylhexanoic acid (116.9 g) and resulting mixture was stirred at 60° C. for about 12 hours. Heptane (161 g) was added to the reaction mixture and separated. The organic layer was extracted with water (80 g). Combined water layer was washed with heptane (161.6 g×3) to give aqueous N-[(S)-methylbenzyl]azetidine-2-(S)-carboxylic acid solution (606.2 g). Yield 94%.

Example 16

A mixture of an aqueous N-[(S)-methylbenzyl]azetidine-2-(S)-carboxylic acid solution (74.21 g., net: 23.7 g), which had been obtained in a similar manner as described in Example 15, and 10% palladium hydroxide on carbon (dry weight: 2.08 g) was stirred under hydrogen atmosphere at 50° C. for 21 hours. Acetic acid (0.76 g) was added to the reaction mixture, kept at the same temperature for 1 hour, and filtered to remove the catalyst. Separated water layer was concentrated under reduced pressure to give a residue, which was dried under reduced pressure to give a white solid of (S)-azetidine-2-carboxylic acid (12.08 g; >99% e.e). Yield 96%.

What is claimed is:

1. Optically active N-(alkylbenzyl)azetidine-2-carboxylic acid represented by the formula (1):

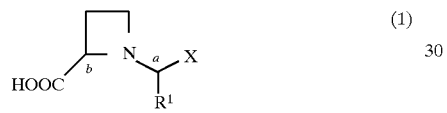

wherein $R^1$ is an alkyl group having 1 to 6 carbon atoms, X is a phenyl group which may be substituted with at least one group selected from a halogen atom, a hydroxyl group, an alkyl group having 1 to 6 carbon atoms and an alkoxy group having 1 to 6 carbon atoms and a and b independently designate asymmetric carbon atoms.

2. A process for producing an optically active azetidine-2-carboxylic acid, which comprises subjecting optically active N-(alkylbenzyl)azetidine-2-carboxylic acid represented by the formula (1) as defined in claim 1 to hydrogenolysis in the presence of a catalyst.

3. A process for producing optically active azetidine-2-carboxylic acid according to claim 2, wherein the hydrogenolysis is carried out using hydrogen, hydrazine or a salt thereof, or formic acid or a salt thereof.

4. A process for preparing optically active azetidine-2-carboxylic acid according to claim 2, wherein the catalyst is platinum on carbon, platinum black, palladium hydroxide on carbon, palladium on carbon, palladium acetate, palladium chloride, palladium oxide or palladium hydroxide.

5. A process for producing the optically active N-(alkylbenzyl)azetidine-2-carboxylic acid as defined in claim 1, which comprises hydrolyzing optically active N-(alkylbenzyl) azetidine-2-carboxylic acid ester represented by the formula (2):

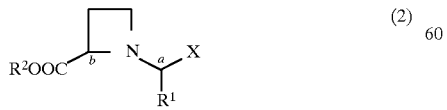

wherein $R^2$ is an aryl group or a saturated hydrocarbon group which may be substituted with an aryl group and X, $R^1$ a and b have the same meaning as defined in claim 1, in the presence of an acid or a base.

6. A process for producing optically active N-(alkylbenzyl) azetidine-2-carboxylic acid ester represented by the formula (2) as defined in claim 5, which comprises the steps of:

(a) contacting the N-(alkylbenzyl) azetidine-2-carboxylic acid ester represented by the formula (2)':

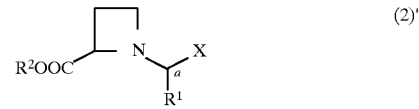

wherein $R^1$, $R^2$, X and a have the same meaning as defined in claim 5, with a dicarboxylic acid of the formula (5):

wherein B is a single bond, a phenylene group,
a straight or branched chain alkylene group which may be substituted with a phenyl group, a hydroxy group which may be protected or a halogen atom,
a cyclic alkylene group which may be substituted with a hydroxy group which may be protected, a halogen atom or a phenyl group, or
a straight or branched chain alkenylene group which may be substituted with a phenyl group, to obtain an adduct of the formula (6):

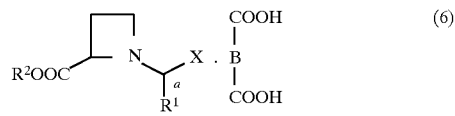

wherein $R^1$, $R^2$, X, B and a have the same meaning as defined above, (b) isolating dicarboxylic acid salt of optically active N-(alkylbenzyl)azetidine-2-carboxylic acid ester represented by the formula (7):

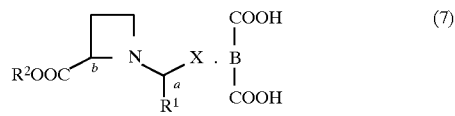

wherein X, B, $R^1$ and $R^2$ have the same meaning as defined above, and a and b, each independently designate asymmetric carbon atom.

(c) treating the obtained salt of the formula (7) with a base.

7. A process for producing optically active N-(alkylbenzyl)azetidine-2-carboxylic acid ester represented by the formula (2) as defined in claim 5, which comprises the steps of:

(a) contacting the N-(alkylbenzyl)azetidine-2-carboxylic acid ester represented by the formula (2)":

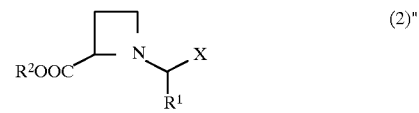

wherein $R^1$, $R^2$ and X have the same meaning as defined above, with a chiral-dicarboxylic acid, (b) isolating a diastereomer salt comprising the chiral dicarboxylic acid and optically active N-(alkylbenzyl)

azetidine-2-carboxylic acid ester represented by the formula (2), and (c) treating the obtained diastereomer salt with a base.

8. A process for producing the optically active N-(alkylbenzyl)azetidine-2-carboxylic acid as defined in claim 1, which comprises the steps of:

(a) contacting the N-(alkylbenzyl)azetidine-2-carboxylic acid ester represented by the formula (2)':

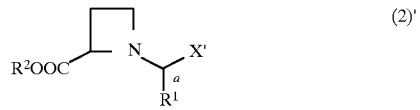

where $R^1$ is an alkyl group having 1 to 6 carbon atoms, X is a phenyl group which may be substituted with at least one group selected from a halogen atom, a hydroxyl group, an alkyl group having 1 to 6 carbon atoms and an alkoxy group having 1 to 6 carbon atoms, a designates an asymmetric carbon atom, $R^2$ is an aryl group or a saturated hydrocarbon group which may be substituted with an aryl group, with a dicarboxylic acid of the formula (5):

wherein B is a single bond, a phenylene group,
a straight or branched chain alkylene group which may be substituted with a phenyl group, a hydroxy group which may be protected or a halogen atom,
a cyclic alkylene group which may be substituted with a hydroxy group which may be protected, a halogen atom or phenyl group, or
a straight or branched chain alkenylene group which may be substituted with a phenyl group, to obtain an adduct of the formula (6):

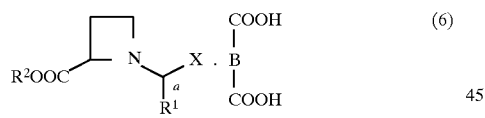

wherein $R^1$, $R^2$, X, B and a have the same meaning as defined above, (b) isolating dicarboxylic acid salt of optically active N-(alkylbenzyl)azetidine-2-carboxylic acid ester represented by the formula (7):

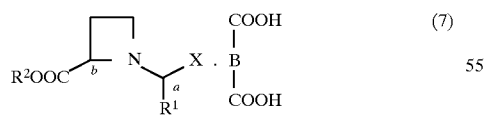

wherein X, B, $R^1$ $R^2$ and a have the same meaning as defined above, and b designates an asymmetric carbon atom, (c) treating the obtained salt of the formula (7) with a base to obtain an optically active N-(alkylbenzyl)azetidine-2-carboxylic acid ester represented by the formula (2):

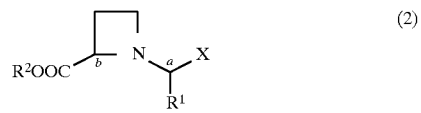

where $R^2$, X, $R^1$, a and b have the same meaning as defined above, and (d) hydrolyzing the compound of the formula (2) in the presence of an acid or a base.

9. A process according to claim 8, wherein the dicarboxylic acid of the formula (5) is selected from an aromatic or aliphatic dicarboxylic acid.

10. A process according to claim 9, wherein the aromatic or aliphatic dicarboxylic acid is selected from oxalic acid, malonic acid, succinic acid, glutaric acid, adipic acid, suberic acid, sebacic acid, camphoric acid, benzylmalonic acid, fumaric acid, maleic acid, acetylenedicarboxylic acid, phthalic acid, isophthalic acid, terephthalic acid, cyclopropanedicarboxylic acid, cyclobutanedicarboxylic acid, cyclopentanedicarboxylic acid, cyclohexanedicarboxylic acid, malic acid, dibenzoyltartaric acid, tartaric acid, camphoric acid, 2,3-dichlorosuccinic acid and 2,3-dibromosuccinic acid.

11. A process for producing optically active N-(alkylbenzyl)azetidine-2-carboxylic acid of the formula (1) as defined in claim 1, which comprises the steps of:

(a) contacting the N-(alkylbenzyl)azetidine-2-carboxylic acid ester represented by the formula (2)'':

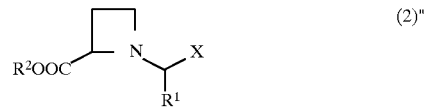

where $R^1$ is an alkyl group having 1 to 6 carbon atoms, X is a phenyl group which may be substituted with at least one group selected from a halogen atom, a hydroxyl group, an alkyl group having 1 to 6 carbon atoms and an alkoxy group having 1 to 6 carbon atoms, $R^2$ is an aryl group or a saturated hydrocarbon group which may be subsituted with an aryl group, with a chiral dicarboxylic acid, (b) isolating a diastereomer salt comprising the chiral dicarboxylic acid and optically active N-(alkylbenzyl) azetidine-2-carboxylic acid ester represented by the formula (2),

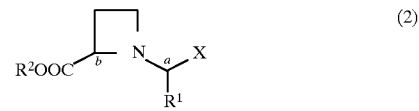

wherein $R^1$, $R^2$ and X are the same as defined above, and a and b designate asymmetric carbon atoms, and (c) treating the obtained diastereomer salt with a base to obtain optically active N-(alkylbenzylazetidine-2-carboxylic acid ester represented by the formula (2) as defined above, and (d) hydrolyzing the compound of the formula (2) in the presence of an acid or a base.

12. A process according to claim 11, wherein the chiral dicarboxylic acid is selected from malic acid, dibenzoyltartaric acid, tartaric acid or camphoric acid.

* * * * *